United States Patent [19]

Vrba

[11] Patent Number: 5,830,512
[45] Date of Patent: *Nov. 3, 1998

[54] INSECT CONTROL COMPOSITIONS

[76] Inventor: Cenek H. Vrba, 213 Cardiff Drive, Calgary, Alberta, Canada, T2K 1S1

[*] Notice: The term of this patent shall not extend beyond the expiration date of Pat. No. 5,122,518.

[21] Appl. No.: 448,357

[22] PCT Filed: Nov. 3, 1992

[86] PCT No.: PCT/CA92/00478

§ 371 Date: Jun. 30, 1995

§ 102(e) Date: Jun. 30, 1995

[87] PCT Pub. No.: WO94/09626

PCT Pub. Date: May 11, 1994

[51] Int. Cl.$^6$ .......................... A01N 59/00; A01N 25/00; A01N 25/04; A01N 25/22
[52] U.S. Cl. .......................... 424/724; 424/600; 424/405; 424/409; 514/937; 514/951
[58] Field of Search ...................................... 424/600, 601, 424/682, 683, 709, 406, 421, 724, 405, 409; 514/63, 937, 951

[56] References Cited

U.S. PATENT DOCUMENTS

| | | | |
|---|---|---|---|
| 3,159,536 | 12/1964 | Marotta | 424/600 |
| 3,764,695 | 10/1973 | Chupp | 514/484 |
| 3,948,636 | 4/1976 | Marks | 71/DIG. 1 |
| 4,071,617 | 1/1978 | Graves et al. | 71/DIG. 1 |
| 5,122,518 | 6/1992 | Vrba | 514/63 |
| B1 3,948,636 | 9/1985 | Marks | 71/DIG. 1 |

*Primary Examiner*—John Pak
*Attorney, Agent, or Firm*—Beveridge, DeGrandi, Weilacher & Young, LLP

[57] ABSTRACT

The invention provides insect control compositions comprising aqueous dispersions of a hydrophobic substance and a hydrophilic substance. The hydrophobic substance is insecticidal or insect-deterring and can be silicon dioxide. The hydrophilic component increases the physico-chemical stability of the dispersion and modifies the textural, visual and/or olfactory characteristics of surfaces to which the compositions are applied; it can be a powdered or finely-divided organic or inorganic substance. The compositions can be applied to plant surfaces by spraying.

22 Claims, No Drawings

INSECT CONTROL COMPOSITIONS

This application is a 371 of PCT/CA92/00478, filed on Nov. 3, 1992.

BACKGROUND OF THE INVENTION

This invention relates to insect control compositions and to methods of using such compositions. In particular, it is directed to environmentally safe compositions in the form of aqueous dispersions which can be applied to plants, soil, animal and human bodies, and other substrates, to control insect pests.

Certain chemically inert dusts or powders of fine particle size are known to be of use in controlling insects. Road dust from dusty roads in orchards has been observed to lower insect populations on trees bordering the roads. Other dusts or powders found to be effective include synthetic and naturally occurring silicious materials, including pyrogenically produced silicas or aerosols, such as AEROSIL (trade mark), CAB-O-SIL (trade mark), Flatting Agent TK 900 (trade mark) and FRANSIL EL (trade mark); ground silicas produced by the wet process, namely precipitated silicas such as ULTRASIL VN3 (trade mark), ZEOSIL (trade mark), HISIL (trade mark), VULCASIL (trade mark) and P 820 (trade mark), silica gels such as SYLOIT (trade mark), GASIL (trade mark) and SORBSIL (trade mark), and aerogels, such as SANTOCEL (trade mark); hydrated aluminum silicates, such as bentonite, montmorillonite and kaolin (bollus alba, china clay, etc.); aluminum magnesium silicates, such as fuller's earth and floridin (a non-plastic variety of kaolin); and finely powdered native hydrous magnesium silicates, such as talc and French chalk. However, such chemically inert powders are of little practical value for controlling insects, especially in agriculture, because they are hydrophilic and of low bulk density. Being hydrophilic, they are readily washed off plant surfaces by rain or if applied as aqueous suspensions, they lose their insecticidal activity entirely. Being of low bulk density, they tend to float far beyond the treated area if applied in dry form.

Chemically inert hydrophilic powders are made more useful for controlling insects by rendering them hydrophobic. Such inert substances may be made hydrophobic by a wide variety of methods known in the art, including treatment with aluminum and zirconium salts of fatty acids, silicone polymers, perfluro compounds, fluorocarbon plasmas, ethoxylated urethanes and sodium oleate. Silicious materials, for example, can be made partially or completely hydrophobic by various methods, including immersion or spraying with an anhydrous solution of hydrophobizing agent, such as an appropriate hydrophobizing organosilicon compound, or exposing the silicious materials to the vapours of a methyl chlorosilane. Methods of preparing hydrophobic silicious materials are known in the art, and are disclosed, for example, in U.S. Pat. No. 3,159,536 (Marotta), issued Dec. 1, 1964.

For convenience of application, particularly in agricultural applications, it is desirable to be able to apply hydrophobic particulate insecticides by spraying aqueous dispersions of them. It is known that e.g. aqueous dispersions of pyrogenically produced and hydrophobic silicas can be used for controlling insect pests, as disclosed in U.S. Pat. No. 5,122,518 to Vrba, issued Jun. 16, 1992. A problem in using such dispersions in agricultural applications is that the dispersion phases (liquid/solid) tend to separate quickly, making uniform spraying more difficult.

It has now been found that aqueous dispersions of a wide variety of hydrophobic insecticidal compositions can be prepared which include naturally occurring substances which both increase the physico-chemical stability of such dispersions and, upon desiccation, modify the visual, textural and/or olfactory stimuli of the surfaces to which the dispersions are applied.

SUMMARY OF THE INVENTION

The insect-controlling compositions of this invention are aqueous dispersions containing a hydrophobic chemically inert powder, such as hydrophobic silica, and a finely divided hydrophilic substance which can be a naturally-occurring organic biodegradable material or an inorganic material.

The purpose of the hydrophobic component is to deter the attacking insects, and having insecticidal effectiveness by itself, it will kill insects providing sufficient period of contact is maintained. The preferred substances are silica dioxides which have been rendered hydrophobic. Suitable products are commercially available hydrophobic silicon dioxide under the trade mark AEROSIL of Degussa AG of Germany, and include AEROSIL R805, AEROSIL R812, AEROSIL R972, AEROSIL 974, et cetera. Other suitable silica products are commercially available hydrophobic silicon dioxide under the trade mark SIPERNAT of Degussa AG, and include SIPERNAT D10 and SIPERNAT D17. Other suitable silica products are hydrophobic silicon dioxide available under the trade mark THICKENER of Wacker AG of Germany, and include THICKENER HDK15, HDK20 and HDK30. The physical and chemical properties of these AEROSIL, SIPERNAT and THICKENER brand silica products are set out in Tables 1, 2 and 3.

TABLE 1

| TESTING METHOD | DIM | AEROSIL R 202 | AEROSIL R 805 | AEROSIL R 812 | AEROSIL R 972 | AEROSIL R 974 |
|---|---|---|---|---|---|---|
| Behaviour towards water | | Hydrophobic | Hydrophobic | Hydrophobic | Hydrophobic | Hydrophobic |
| Surface according to BET[1)] | $m^2/g$ | 90 ± 20 | 150 ± 25 | 260 ± 30 | 110 ± 20 | 170 ± 20 |
| Average size of the primary particles | nanometers | 14 | 12 | 7 | 16 | 12 |
| Stamping density[2)] | | | | | | |
| Normal product | g/l | ca. 50 | ca. 50 | ca. 50 | ca. 50 | ca. 50 |
| Compressed product (additive "V") | g/l | ca. 90 | ca. 90 | ca. 90 | ca. 90 | ca. 90 |
| Drying loss[3)] (2 hours at 105° C. upon leaving the supplier) | % | <0.5 | <0.5 | <0.5 | <0.5 | <0.5 |

TABLE 1-continued

| TESTING METHOD | DIM | AEROSIL R 202 | AEROSIL R 805 | AEROSIL R 812 | AEROSIL R 972 | AEROSIL R 974 |
|---|---|---|---|---|---|---|
| Ignition loss[4) 7)] (2 hours at 1000° C.) | % | 4.5–7.5[13)] | 6.0–9.0[14)] | 1.0–2.5[15)] | <2[12)] | <2[12)] |
| pH[5)] (in 4% aqueous dispersion) |  | 4.0–6.0[10)] | 3.5–5.5[10)] | 5.5–7.5[10)] | 3.6–4.3[10)] | 3.4–4.2[10)] |
| $SiO_2$[8)] | % | >99.8 | >99.8 | >99.8 | >99.8 | >99.8 |
| $Al_2O_3$[8)] | % | <0.05 | <0.05 | <0.05 | <0.05 | <0.05 |
| $Fe_2O_3$[8)] | % | <0.01 | <0.01 | <0.01 | <0.01 | <0.01 |
| $TiO_2$[8)] | % | <0.03 | <0.03 | <0.03 | <0.03 | <0.03 |
| HCl[8) 11)] | % | <0.025 | <0.025 | <0.025 | <0.05 | <0.01 |
| Sieve residue[6)] (according to Mocker, 45 um) | % | — | — | — | — | — |

[1)]according to DIN 66 131
[2)]according to DIN ISO 787/XI, JIS K 5101/18
[3)]according to DIN ISO 787/II, ASTM D 280, JIS K 5101/21
[4)]according to DIN 55 921, ASTM D 1208, JIS K 5101/23
[5)]according to DIN ISO 787/IX, ASTM D 1208, JIS K 5101/24
[6)]according to DIN ISO 787/XVII, JIS K 5101/20
[7)]relative to the substance dried 2 hours at 105° C.
[8)]relative to the substance annealed 2 hours at 1000° C.
[9)]special anti-moisture packaging
[10)]in water: acetone or methanol = 1:1
[11)]HCl content is a component of the ignition loss
[12)]contains approximately 1% chemically bound carbon
[13)]contains approximately 5% chemically bound carbon
[14)]contains approximately 7% chemically bound carbon
[15)]contains approximately 3.5% chemically bound carbon These silicas can be produced according to known methods, for example according to DE-PS 11 63 784.

TABLE 2

PHYSICAL AND CHEMICAL PROPERTIES

|  |  | Sipernat ® D10 | Sipernat ® D17 |
|---|---|---|---|
| BET Surface Area[1)] | m²/g | 90 | 100 |
| Average Agglomerate Size[2)] | μm | 5 | 10 |
| Topped Density[3)] | g/l | 100 | 150 |
|  | lbs/c.ft. | 6.2 | 9.4 |
| pH[4)] |  | 10.3[9)] | 8[9)] |
| DBP Absorption | % | 240 | 230 |
| Sieve Residue (acc. Mocker 45 μm)[5)] | % | 0.01 | 0.1 |
| Moisture[6)] (2 hours at 105° C.) | % | 3 | 3 |
| Ignition loss[6) 7)] (2 hours at 1000° C.) | % | 7[10)] | 7[11)] |
| $SiO_2$[8)] | % | 98 | 99.5 |
| $Na_2O$[8)] | % | 0.8 | 0.2 |
| $Fe_2O_3$[8)] | % | 0.03 | 0.03 |
| $SO_3$[8)] | % | 0.8 | 0.1 |

[1)]DIN 66 131
[2)]Measured by Coulter Counter ® (100 μm aperture)
[3)]DIN 53 194 (without sieving) or ISO 787/X1
[4)]DIN 53 200 (in a 5% silica/water dispersion) or ASTM D 1208 or ISO 787/1X
[5)]DIN 53 580 or ISO 787/XVIII
[6)]DIN 55 921 or ASTM D 1208
[7)]Based on material dried for 2 hours at 105° C.
[8)]Based on material ignited for 2 hours at 1000° C.
[9)]In water:methanol = 1:1
[10)]Contains approx. 3% chemically bonded carbon
[11)]Contains approx. 2% chemically bonded carbon

TABLE 3

PHYSICAL AND CHEMICAL PROPERTIES OF THICKENER ® (WACKER) HDK 15, 20 AND 30

| Type | HDK 15 | HDK 20 | HDK 30 |
|---|---|---|---|
| Surface area by BET measurement (m²/g)(DIN66131) | 120 ± 20 | 170 ± 30 | 250 ± 30 |
| $SiO_2$ - content (% w/w)[1)] (DIN55921) | >99.8 | >99.8 | >99.8 |
| Apparent density, uncompressed (g/l) (DIN ISO 787/11) | approx. 40 | approx. 40 | approx. 40 |
| Apparent density, P-compressed (g/l) (DIN ISO 787/11) | approx. 90 | approx. 90 |  |
| Moisture content (% w/w)[2)] 2 hrs. at 105° C. (DIN ISO 787/2) | <0.6 | <0.6 | <0.6 |
| Loss on ignition (% w/w)[3)] 2 hrs. at 1000° C. (DIN 52911) | <2 | <2 | <2 |
| pH-value in 4% $H_2O$ dispersion (DIN ISO 787/9) | 4.0–4.8[4)] | 4.0–4.8[4)] | 4.0–4.8[4)] |
| Sieve residue > 40 μm (% w/w) (DIN 53580) | <0.05 | <0.05 | <0.05 |
| HCl (% w/w)[1)] | <0.02 | <0.02 | <0.05 |
| $Al_2C_3$ (% w/w)[1)] | <0.05 | <0.05 | <0.05 |
| $Fe_2O_3$ (% w/w)[1)] | <0.005 | <0.005 | <0.005 |
| $TiO_2$ (% w/w)[1)] | <0.003 | <0.003 | <0.003 |
| C (% w/w) | <2 | <2.1 | <2.2 |

[1)]The figures quoted relate to the substance heated at 1000° C. for two hours.
[2)]When leaving the plant site.
[3)]The figures quoted relate to the substance dried at 105° C. for two hours.
[4)]4% dispersion in a 1:1 mixture of water and methanol.

The preferred weight percent range of the hydrophobic component in the dispersions is about 2–3%.

The preferred particle size of the hydrophobic component is about 5–40 nanometers.

Being chemically inert, the hydrophobic component does not react with other components and can therefore be combined with many other constituents in the aqueous dispersions of the invention.

The hydrophilic component has two primary purposes. One is to increase the physico-chemical stability of the aqueous dispersion, i.e. to slow its separation into the aqueous and solid phases so it can be applied relatively uniformly by conventional spraying equipment. The hydrophobic component is not intended to affect the chemical stability of the dispersions, since they are chemically stable.

The other purpose of the hydrophilic component is to adhere to the sprayed surfaces, eg. plants, soil, etc., after the dispersion is applied and dries, in order to modify the visual, textural and/or olfactory characteristics of surfaces to which the compositions are applied. This changes the visual, textural, olfactory and/or chemical stimuli received by insects seeking to feed or lay eggs on the sprayed substrate, thus disorienting and confusing the insects, i.e. impeding their recognition of the sprayed plant, etc. The effect is to delay or inhibit the feeding and ovipositioning of insects on plants, etc. on which they would otherwise feed. Thus, hydrophilic materials are selected which have both these properties. Such materials may be referred to as dissimulantia (materials used to disguise something under a feigned appearance) or latebrantia (materials used to dissemble the real nature of a thing).

It is believed that the hydrophilic materials used in the invention also enhance the adhesion of the insecticide to the substrates upon desiccation of the dispersion by forming uniformly coated, drift-proof protecting surfaces. The compositions of the invention accordingly do not pose a health hazard to humans or animals since they release the small particles of the hydrophobic substance only upon mechanical contact by insects, and adhere to the insect bodies.

The hydrophilic component can be a natural organic biodegradable material, such as bagasse, bark, bone meal, burlap, casein, charcoal, cellulose, cork, duff, cotton wool, feathers, leaves, non-fat powdered milk, paper, peat moss, tang, sawdust, seaweed, straw, whey, yeast, wood flour, starch and oyster shells. Many of these materials can be ground to a fine powder, and such materials are used in that form in the invention. The preferred particle size of such materials is less than about 355 $\mu$m (U.S. sieve size 45) and especially less than about 125 $\mu$m (U.S. sieve size 120). This can be accomplished by dehydrating the materials where necessary, for example, by freeze-drying, and by milling to the desired particle size. Others of the hydrophilic materials are fibrous and cannot readily be reduced to a powder, for example, paper, burlap, cotton-wool, etc. Such materials are reduced by shredding or similar processes to small fibers for use in the invention.

Alternatively, the hydrophilic component can be an inorganic material in powder form, such as fuller's earth, bentonite, sparcoloid, talc, kaolin, Alberta slip, silica flint, bone ash, E.P.K. (Edgar Plastic Kaolin), dolomite, pyrophilite, Old Mining #4 ballclay, volcanic ash, nepheline syenite, calcium carbonate, cluster feldspar, pumice, chalk, vermiculite, CELITE 209 (natural diatomaceous earth -DE- amorphous silica (trade mark), MICROCELL E (synthetic hydrous calcium silicate ) (trade mark), CELKATE T21 (synthetic magnesium silicate) (trade mark), SUPERFLOSS (flux calcined diatomite) (trade mark), CELITE R685 (synthetic sylicate biocatalyst) (trade mark), and diatomaceous earth, such as ZORBALL (trade mark) and DRY-FIOOR (trade mark). For use in the invention, these materials are rendered in a powder form of relatively fine particle size. Preferably, they are less than about 125 $\mu$m.

Organic hydrophilic materials are preferred to inorganic hydrophilic materials for use in the invention, in part because inhalation of the product during application is possible, and it is preferable to avoid inhalation of inorganic powders; and in part because the inorganic materials tend to build sediments in aqueous dispersions and result in a less uniform product during application (cf. *Handbook of Pesticide Toxicology*, Weyland J. Hayes Jr. and Edward R. Laws Jr., Academic Press Inc., 1990).

A broad range of weight percentages of the hydrophilic component in the aqueous dispersions can be employed; the preferred weight percent is about 2–5%. A combination of two or more of the hydrophilic materials can be employed in the compositions.

In addition to the hydrophobic ingredient, the hydrophilic ingredient and water, other substances may be included in the aqueous dispersions of the invention. Pigments and spices can be added so that the color and smell of the sprayed surfaces after the product dries will be altered as desired. This can further disguise the normal olfactory and visual stimuli an insect receives from the sprayed plant, and thus help deter the insect. To alter the color of the product, natural and synthetic dyes or pigments and combinations of them can be used, for example, chlorophyll, xantophyl and saffron. Smell can be modified by using rotting peat moss or spices, such as sage, curry, allspice, thyme, anise, cinnamon, oregano, cloves, ginger, black pepper, chili, celery seed, nutmeg, dill seed, onion, garlic, horse radish, cayenne and green pepper. Combinations of particular spices, colors and hydrophilic components can be used in the invention to best deter specific types of insects, according to the particular instincts and behaviours (eg. orientation, feeding, egg-laying, search senses, etc.) of specific insects.

In addition, other pest control products can be included in the aqueous dispersions of the invention, including, for example, fungicides, anthelmintics, and insecticides such as botanicals, biologicals, attractants, repellants and sterilants.

DETAILED DESCRIPTION OF THE PREFERRED EMBODIMENTS

The following compositions were prepared according to the invention.

EXAMPLE 1

10 g of pine bark flour, particle size smaller than 355 $\mu$m (U.S. sieve size 45) and 10 g of AEROSIL R805, blended with 380 g of water for 15 to 20 minutes in a high-speed blender (over 2000 r.p.m.). The dispersing agent is blended with the water first, and AEROSIL is added subsequently; otherwise, an unsatisfactory quality dispersion results. 0.5 ml liquid food color added two minutes before end of mixing. (Food color preparation-1990 Reg. Can. T. M. McCormic Canada Inc.) Any non-toxic, synthetic or natural pigment substance can be used for coloring. Dispensed into glass containers for further use. Final concentration of bark flour is 2.5%; of Aerosil R805 is 2.5%.

EXAMPLE 2

5 g of pine bark flour, particle size smaller than 125 $\mu$m (U.S. sieve size 120) and 5 g of AEROSIL R805, blended with 190 g of water for 15 to 20 minutes in a high-speed blender. Dispensed into glass containers for further use. Final concentration of bark flour is 2.5%; of AEROSIL R805 is 2.5%.

EXAMPLE 3

5 g of pine bark flour of the same designation as in Example 2, and 5 g of SIPERNAT D10, blended with 190 g of water for 15 to 20 minutes in a high-speed blender. The resulting dispersion concentration and handling as in Example 2.

EXAMPLE 4

5 g of pine bark flour of the same designation as in Example 2, and 5 g of SIPERNAT D17, blended with 190 g of water for 15 to 20 minutes in a high-speed blender. The resulting dispersion concentration and handling as in Example 2.

EXAMPLE 5

5 g of pine bark flour of the same designation as in Example 2, and 5 g of THICKENER HDK15, blended with 190 g of water for 15 to 20 minutes in a high-speed blender. The resulting dispersion concentration and handling as in Example 2.

EXAMPLE 6

5 g of pine bark flour of the same designation as in Example 2, and 5 g of THICKENER HDK20, blended with 190 g of water for 15 to 20 minutes in a high-speed blender. The resulting dispersion concentration and handling as in Example 2.

EXAMPLE 7

5 g of pine bark flour of the same designation as in Example 2, and 5 g of THICKENER HDK30, blended with 190 g of water for 15 to 20 minutes in a high-speed blender. The resulting dispersion concentration and handling as in Example 2.

EXAMPLE 8

10 g of ground peat moss, particle size smaller than 355 $\mu$m as in Example 1, and 10 g of AEROSIL R805, blended with 380 g of water for 15 to 20 minutes in a high-speed blender. The resulting dispersion concentration and handling as in Example 1.

EXAMPLE 9

10 g of ground saw dust, particle size smaller than 355 $\mu$m as in Example 1, and 10 g of AEROSIL R805, blended with 380 g of water for 15 to 20 minutes in a high-speed blender. The resulting dispersion concentration and handling as in Example 1.

EXAMPLE 10

10 g of shredded scrap newspaper and 10 g of AEROSIL R805, blended with 600 g of water for 15 to 20 minutes in a high-speed blender. The resulting dispersion is thick and contains about 1.6% of paper and 1.6% of AEROSIL R805 and is handled as in Example 1.

EXAMPLE 11

1 g of shredded scrap newspaper and 6 g of AEROSIL R805, blended with 193 g of water for 15 to 20 minutes in a high-speed blender. The resulting dispersion contains 0.5% of paper and 3% of AEROSIL R805 and is handled as in Example 1.

EXAMPLE 12

1 g of shredded scrap newspaper and 6 g of AEROSIL R805, blended with 193 g of water for 15 to 20 minutes in a high-speed blender and 0.2 ml of food coloring as designated in Example 1. The resulting dispersion concentration as in Example 11 and handling as in Example 1.

EXAMPLE 13

1 g of straw flour, particle size smaller than 355 $\mu$m as in Example 1, and 6 g of AEROSIL R805 blended with 193 g of water for 15 to 20 minutes in a high-speed blender. The resulting dispersion concentration as in Example 11 and handling as in Example 1.

EXAMPLE 14

1 g of non-bonded paper (shredded paper egg cartons) and 6 g of AEROSIL R805 blended with 193 g of water for 15 to 20 minutes in a high-speed blender. Food coloring added as in Example 12. The resulting dispersion concentration as in Example 11 and handling as in Example 1.

EXAMPLE 15

1 g of non-bonded paper as in Example 14 and 6 g of AEROSIL R805 blended with 193 g of water for 15 to 20 minutes in a high-speed blender, no food coloring added. The resulting dispersion concentration as in Example 11 and handling as in Example 1.

EXAMPLE 16

2 g of shredded cotton wool and 6 g of AEROSIL R805 blended with 192 g of water in a high-speed blender, food coloring added as in Example 14. The resulting dispersion concentration is 1% cotton wool and 3% AEROSIL R805. Handling as in Example 1.

EXAMPLE 17

1 g of shredded scrap newspaper and 6 g of AEROSIL R805 blended with 193 g of water for 15 to 20 minutes in a high-speed blender, no food coloring added. The resulting dispersion concentration as in Example 11 and handling as in Example 1.

EXAMPLE 18

5 g of shredded burlap and 5 g of AEROSIL R805, blended with 240 g of water for 15 to 20 minutes in a high-speed blender, food coloring added as in Example 12. The resulting dispersion is thick and contains 2% burlap and 2% AEROSIL R805 and is handled as in Example 1.

EXAMPLE 19

5 g of shredded burlap and 5 g of AEROSIL R805, blended with 240 g of water for 15 to 20 minutes in a high-speed blender, no food coloring added. The resulting dispersion is thick and contains 2% burlap and 2% AEROSIL R805 and is handled as in Example 1.

EXAMPLE 20

1 g of seaweed flour, particle size smaller than 125 $\mu$m, same as in Example 2, and 6 g of AEROSIL R805 blended with 193 g of water for 15 to 20 minutes in a high-speed blender. (No food coloring necessary due to presence of natural pigment.) The resulting dispersion concentration contains 0.5% of seaweed flour and 3% of AEROSIL R805 and is handled as in Example 1.

EXAMPLE 21

2 g of talc (Fisher) and 2 g of AEROSIL R805 blended with 196 g of water for 15 to 20 minutes in a high-speed blender. The resulting dispersion concentration of talc is 1% and of AEROSIL R805 is 1% and is handled as in Example 1.

EXAMPLE 22

2 g of fuller's earth (bentonite or sparcolloid) and 2 g of AEROSIL R805 blended with 196 g of water for 15 to 20 minutes in a high-speed blender. The resulting dispersion concentration of fuller's earth is 1% and of AEROSIL R805 is 1% and is handled as in Example 1.

EXAMPLE 23

2 g of CELITE 209 (Mannville) and 2 g of AEROSIL R805 blended with 196 g of water for 15 to 20 minutes in a high-speed blender. The resulting dispersion concentration of CELITE 209 is 1% and of AEROSIL R805 is 1% and is handled as in Example 1.

EXAMPLE 24

2 g of MICROCELL E (Mannville) and 2 g of AEROSIL R805 blended with 196 g of water for 15 to 20 minutes in a high-speed blender. The resulting dispersion concentration of MICROCELL A is 1% and of AEROSIL R805 is 1% and is handled as in Example 1.

EXAMPLE 25

2 g of ZORBALL (diatomaceous earth) and 2 g of AEROSIL R805 blended with 196 g of water for 15 to 20 minutes in a high-speed blender. The resulting dispersion concentration of ZORBALL is 1% and of AEROSIL R805 is 1% and is handled as in Example 1.

EXAMPLE 26

2 g of DRYFLOOR (diatomaceous earth) and 2 g of AEROSIL R805 blended with 196 g of water for 15 to 20 minutes in a high-speed blender. The resulting dispersion concentration of DRYFLOOR is 1% and of AEROSIL R805 is 1% and is handled as in Example 1.

Experiments were conducted to test the effectiveness as insecticides of the compositions prepared in accordance with the invention. Tribolium confusum (Duval) (flour beetles) were reared in a darkened room at 21±2° C. and 35–45% relative humidity on a medium consisting of 95% whole wheat flour and 5% brewer's yeast. Aqueous dispersions according to the invention were measured out into Petri dishes and were dried or dehydrated for 48 hours before testing for insecticidal action. Adult beetles, about eight days of age, were separated from their medium with a suitable sieve and transferred to the Petri dishes (5×1 cm) by oral suction, and their mortality over time was observed. The results are summarized in Table 4.

TABLE 4

CUMULATIVE MORTALITY OF *TRIBOLIUM CONFUSUM* (DUV.) (FLOUR BEETLE)
CONTINUOUS EXPOSURE TO AQUEOUS DISPERSIONS AFTER DEHYDRATION

| No. | MATERIAL TESTED - DOSAGE | NO. OF INSECTS | CUMUL. MORTALITY % IN DAYS | | | | | | | | | | NOTES |
|---|---|---|---|---|---|---|---|---|---|---|---|---|---|
| | | | 1 | 2 | 3 | 4 | 5 | 6 | 7 | 8 | 9 | 10 | |
| 1 | AEROSIL R805 (as pure dry powder) - 30 mg/dish (3 dishes) | 90 | 97 | 100 | | | | | | | | | |
| 2 | AEROSIL R805 - 5% dry water - 30 mg/dish (3 dishes) | 90 | 100 | | | | | | | | | | |
| 3 | Untreated controls without food | 30 | 0 | 0 | 0 | 0 | 0 | 0 | 0 | 0 | 0 | 0 | 10% 12th day |
| 4 | AEROSIL R805 - 2% aqueous dispersion - 30 mg/dish (2 dishes) | 60 | 52 | 98 | 100 | | | | | | | | |
| 5 | Untreated controls with food | 30 | 0 | 0 | 0 | 0 | 0 | 0 | 0 | 0 | 0 | 0 | 10% 24th day |
| 6 | AEROSIL R805 - 3% aqueous dispersion - 30 mg/dish (3 dishes) | 90 | 54 | 99 | 100 | | | | | | | | |
| 7 | Untreated controls without food | 90 | 0 | 0 | 0 | 0 | 0 | 0 | 0 | 2 | 2 | 2 | |
| 8 | Composition per Example 1 - 3 ml/dish (3 dishes) | 90 | 84 | 100 | | | | | | | | | |
| 9 | Same as no. 8 - after rinsing and drying (3 dishes) | 90 | 97 | 100 | | | | | | | | | |
| 10 | Same as no. 8 - after rinsing and drying (3 dishes) | 90 | 91 | 100 | | | | | | | | | |
| 11 | Same as no. 8 - after rinsing and drying (3 dishes) | 90 | 61 | 100 | | | | | | | | | |
| 12 | Same as no. 8 - after rinsing and drying (3 dishes) | 90 | 30 | 100 | | | | | | | | | |
| 13 | Composition per Example 1, without food color - 3 ml/dish (3 dishes) | 90 | 68 | 100 | | | | | | | | | |
| 14 | Same as no. 13 - after rinsing and drying (3 dishes) | 90 | 87 | 100 | | | | | | | | | |
| 15 | Same as no. 13 - after rinsing and drying (3 dishes) | 90 | 94 | 100 | | | | | | | | | |
| 16 | Same as no. 13 - after rinsing and drying (3 dishes) | 90 | 77 | 100 | | | | | | | | | |
| 17 | Same as no. 13 - after rinsing and drying (3 dishes) | 90 | 39 | 100 | | | | | | | | | |
| 18 | Composition per Example 2 - 3 ml/dish (3 dishes) | 90 | 65 | 100 | | | | | | | | | |
| 19 | Same as no. 18 - after rinsing and drying (3 dishes) | 90 | 43 | 100 | | | | | | | | | |
| 20 | Untreated controls without food | 90 | 0 | 0 | 0 | 0 | 0 | 0 | 0 | 0 | 0 | 0 | 3% 15th day |
| 21 | SIPERNAT D10 (as pure dry powder) - 30 mg/dish (3 dishes) | 90 | 47 | 100 | | | | | | | | | |
| 22 | SIPERNAT D10 - 5% dry water - 30 mg/dish (3 dishes) | 90 | 1 | 93 | 100 | | | | | | | | |
| 23 | Composition per Example 3 - 30 ml/dish (3 dishes) | 90 | 0 | 100 | | | | | | | | | |

TABLE 4-continued

CUMULATIVE MORTALITY OF *TRIBOLIUM CONFUSUM* (DUV.) (FLOUR BEETLE)
CONTINUOUS EXPOSURE TO AQUEOUS DISPERSIONS AFTER DEHYDRATION

| No. | MATERIAL TESTED - DOSAGE | NO. OF INSECTS | CUMUL. MORTALITY % IN DAYS ||||||||||  NOTES |
|---|---|---|---|---|---|---|---|---|---|---|---|---|---|
| | | | 1 | 2 | 3 | 4 | 5 | 6 | 7 | 8 | 9 | 10 | |
| 24 | SIPERNAT D17 (as pure dry powder) - 30 mg/dish (3 dishes) | 90 | 47 | 100 | | | | | | | | | |
| 25 | Untreated controls without food | 30 | 0 | 0 | 0 | 0 | 0 | 0 | 0 | 0 | 0 | 0 | 3% 11th day |
| 26 | SIPERNAT D17 - 10% dry water - 30 mg/dish (3 dishes) | 90 | 10 | 86 | 99 | 100 | | | | | | | |
| 27 | Composition per Example 4 - 30 ml/dish (3 dishes) | 90 | 0 | 88 | 100 | | | | | | | | |
| 28 | Untreated controls without food | 90 | 0 | 0 | 0 | 0 | 0 | 0 | 0 | 0 | 0 | 0 | 3% 11th day |
| 29 | HDK15 (as pure dry powder) - 30 mg/dish (3 dishes) | 90 | 50 | 100 | | | | | | | | | |
| 30 | HDK15 - 2% aqueous suspension - 30 ml/dish (3 dishes) (dried one hour) | 90 | 0 | 74 | 100 | | | | | | | | |
| 31 | Composition per Example 5 - 30 ml/dish (3 dishes) | 90 | 0 | 36 | 68 | 92 | 100 | | | | | | |
| 32 | HDK20 (as pure dry powder) - 30 mg/dish (3 dishes) | 90 | 94 | 100 | | | | | | | | | |
| 33 | HDK20 - 2% aqueous suspension - 30 ml/dish (3 dishes) (dried one hour) | 90 | 0 | 10 | 74 | 93 | 97 | 100 | | | | | |
| 34 | Composition per Example 6 - 30 ml/dish (3 dishes) | 90 | 0 | 4 | 47 | 92 | 100 | | | | | | |
| 35 | HDK30 (as pure dry powder) - 30 mg/dish (3 dishes) | 90 | 0 | 100 | | | | | | | | | |
| 36 | HDK30 - 2% aqueous suspension - 30 ml/dish (3 dishes) (dried one hour) | 90 | 1 | 80 | 99 | 100 | | | | | | | |
| 37 | Composition per Example 7 - 30 ml/dish (3 dishes) | 90 | 0 | 5 | 37 | 79 | 94 | 100 | | | | | |
| 38 | Untreated controls without food | 90 | 0 | 0 | 0 | 0 | 0 | 0 | 0 | 0 | 0 | 0 | 3% 15th day |
| 39 | Composition per Example 8 - 3 ml/dish (3 dishes) | 90 | 0 | 93 | 100 | | | | | | | | |
| 40 | Same as no. 39, after rinsing (3 dishes) | 90 | 0 | 51 | 100 | | | | | | | | |
| 41 | Same as no. 39, after rinsing (3 dishes) | 90 | 8 | 93 | 100 | | | | | | | | |
| 42 | Composition per Example 9 - 3 ml/dish (3 dishes) | 90 | 23 | 100 | | | | | | | | | |
| 43 | Composition per Example 10 - Stained 3 ml/dish (3 dishes) | 90 | 0 | 0 | 2 | 10 | 77 | 97 | 100 | | | | |
| 44 | Composition per Example 12 - 3 ml/dish (3 dishes) | 90 | 0 | 3 | 80 | 99 | 100 | | | | | | |
| 45 | Composition per Example 11 - Unstained 3 ml/dish (3 dishes) | 90 | 0 | 40 | 88 | 97 | 99 | 100 | | | | | |
| 46 | Composition per Example 13, with food color - Stained 3 ml/dish (3 dishes) | 90 | 0 | 8 | 44 | 97 | 99 | 100 | | | | | |
| 47 | Composition per Example 13 - 3 ml/dish (3 dishes) | 90 | 0 | 14 | 87 | 97 | 100 | | | | | | |
| 48 | Composition per Example 14 - 3 ml/dish (3 dishes) | 90 | 23 | 58 | 100 | | | | | | | | |
| 49 | Composition per Example 15 - 3 ml/dish (2 dishes) | 60 | 90 | 100 | 100 | | | | | | | | |
| 50 | Composition per Example 16 - Stained 3 ml/dish (3 dishes) | 90 | 19 | 99 | 100 | | | | | | | | |
| 51 | Composition per Example 16, without food color 3 ml/dish (3 dishes) | 90 | 18 | 99 | 100 | | | | | | | | |
| 52 | Composition per Example 18 - 3 ml/dish (3 dishes) | 90 | 0 | 38 | 100 | | | | | | | | |
| 53 | Composition per Example 19 - 3 ml/dish (3 dishes) | 90 | 6 | 91 | 100 | | | | | | | | |
| 54 | Composition per Example 20 - 3 ml/dish (3 dishes) | 90 | 0 | 3 | 56 | 86 | 91 | 100 | | | | | |
| 55 | Untreated controls without food | 90 | 0 | 0 | 0 | 0 | 0 | 0 | 0 | 0 | 0 | 0 | 3% 15th day |
| 56 | 2% Talc (Fisher) suspension - 3 ml/dish | 30 | 0 | 7 | 17 | 43 | 67 | 70 | 73 | 83 | 93 | 93 | 100% 12th day |
| 57 | Composition per Example 21 - 3 ml/dish | 30 | 33 | 100 | | | | | | | | | |
| 58 | Same as no. 57, after 1st rinsing | 30 | 37 | 100 | | | | | | | | | |
| 59 | Same as no. 57, after 2nd rinsing | 30 | 20 | 93 | 100 | | | | | | | | |
| 60 | Same as no. 57, after 3rd rinsing | 30 | 3 | 67 | 100 | | | | | | | | |
| 61 | Same as no. 57, after 4th rinsing | 30 | 3 | 70 | 100 | | | | | | | | |
| 62 | Same as no. 57, after 5th rinsing | 30 | 0 | 60 | 97 | 100 | | | | | | | |
| 63 | Same as no. 57, after 6th rinsing | 30 | 0 | 20 | 97 | 100 | | | | | | | |
| 64 | Same as no. 57, after 7th rinsing | 30 | 0 | 0 | 40 | 90 | 97 | 100 | | | | | |
| 65 | Same as no. 57, after 8th rinsing | 30 | 0 | 7 | 77 | 100 | | | | | | | |

TABLE 4-continued

CUMULATIVE MORTALITY OF *TRIBOLIUM CONFUSUM* (DUV.) (FLOUR BEETLE)
CONTINUOUS EXPOSURE TO AQUEOUS DISPERSIONS AFTER DEHYDRATION

| No. | MATERIAL TESTED - DOSAGE | NO. OF INSECTS | 1 | 2 | 3 | 4 | 5 | 6 | 7 | 8 | 9 | 10 | NOTES |
|---|---|---|---|---|---|---|---|---|---|---|---|---|---|
| 66 | Same as no. 57, after 9th rinsing | 30 | 0 | 0 | 7 | 23 | 67 | 87 | 97 | 100 | | | |
| 67 | Same as no. 57, after 10th rinsing | 30 | 0 | 0 | 0 | 30 | 87 | 100 | | | | | |

NOTE:
All dispersions dried or dehydrated for 48 hours.

In Table 4, the expression "dry water" means a dispersion of up to 95% of water (liquid phase) in AEROSIL (solid phase). Using a high-speed blender, small water droplets are covered and enfolded in a layer of small particles of hydrophobic silica, which prevents the droplets from uniting back into a continuous liquid phase.

Where samples are indicated as being rinsed, the desiccated compositions in the Petri dishes were rinsed with about 100 ml of cold tap water from a distance of 15–20 cm in three successions.

The physical stability of the aqueous dispersions prepared in accordance with the invention was tested, and the results are summarized in Table 5. The presence of the hydrophilic component in the dispersion significantly delayed the time that the first sign of separation of the dispersion was observed.

In Tables 5 and 6, "<45" and "<120" refers to a particles of a size which pass through a sieve of U.S. sieve designation 45 (355 $\mu$m) and 120 (125 $\mu$m) respectively. "Stained" and "unstained" refer to the presence or absence of food coloring in the composition.

The effect of aqueous dispersions according to the invention and aqueous dispersions of certain of the hydrophilic components only on deterring insects was studied, and the results are summarized in Table 6. It was observed that the hydrophilic component on its own had a significant effect in deterring insects, relative to the untreated controls.

TABLE 5

STABILITY OF COMPOSITIONS - SEPARATION OF PHASES

| No. | COMPOSITION TESTED | FIRST SIGN OF SEPARATION OF PHASES (IN MINUTES) | % OF SEPARATION (IN HOURS) 2 HOURS | 48 HOURS |
|---|---|---|---|---|
| 1 | AEROSIL R805 4 g, H$_2$O 196 g (2% Aqueous dispersion) | 2 | 29% | 33% |
| 2 | AEROSIL R202 4 g, H$_2$O 196 g (2% Aqueous dispersion) | 0.5 | 36% | 40% |
| 3 | AEROSIL R812 4 g, H$_2$O 196 g (2% Aqueous dispersion) | 2 | 31% | 36% |
| 4 | AEROSIL R972 4 g, H$_2$O 196 g (2% Aqueous dispersion) | 3 | 35% | 42% |
| 5 | Composition per Example 14 - Stained | 20 | 20% | 25% |
| 6 | Composition per Example 12 - Stained | 15 | 33% | 44% |
| 7 | Composition per Example 17 - Unstained | 25 | 20% | 32% |
| 8 | Composition per Example 8, with food color | 20 | 21% | 29% |
| 9 | Composition per Example 8 | 20 | 9% | 23% |
| 10 | Straw <45 10 g, AEROSIL R805 10 g, H$_2$O 380 g - Stained | 15 | 28% | 39% |
| 11 | Straw <45 10 g, AEROSIL R805 10 g, H$_2$O 380 g - Unstained | 20 | 20% | 38% |
| 12 | Composition per Example 1 | 15 | 23% | 39% |
| 13 | Composition per Example 1, without food color | 15 | 23% | 37% |
| 14 | Tree Bark <45 4 g, AEROSIL R202 4 g, H$_2$O 192 g - Unstained | 2 | 30% | 36% |
| 15 | Tree Bark <45 4 g, AEROSIL R812 4 g, H$_2$O 192 g - Unstained | 3.5 | 23% | 32% |
| 16 | Tree Bark <45 4 g, AEROSIL R972 4 g, H$_2$O 192 g - Unstained | 14 | 21% | 27% |
| 17 | Tree Bark <120 5 g, AEROSIL R805 4 g, H$_2$O 190 g - Unstained | 15 | 23% | 31% |
| 18 | Composition per Example 9, with food color | 12 | 35% | 38% |
| 19 | Composition per Example 9 | 15 | 33% | 47% |
| 20 | Composition per Example 18 | 20 | 38% | 43% |
| 21 | Composition per Example 16, without food color | 20 | 33% | 33% |
| 22 | Starch 5 g, AEROSIL R805 5 g, H$_2$O 190 g - Unstained | 30 | 17% | 26% |
| 23 | Composition per Example 20 | 60 | 25% | 25% |
| 24 | THICKENER HDK15 2% Aqueous Suspension - Unstained | 20 | 20% | 38% |
| 25 | THICKENER HDK20 2% Aqueous Suspension - Unstained | 20 | 10% | 30% |
| 26 | THICKENER HDK30 2% Aqueous Suspension - Unstained | 25 | 10% | 20% |
| 27 | THICKENER HDK30 6 g, AEROSIL R805 6 g, H$_2$O 380 g - Unstained | 25 | 15% | 36% |

TABLE 6

NUMBER OF INSECTS*) SETTLED ON DRY FLOUR CAKES**) TREATED WITH VARIOUS COMPOSITIONS.
(100 INSECTS USED)

| No. | COMPOSITION TESTED | DAYS | | | | | | | | | | TOTAL |
|---|---|---|---|---|---|---|---|---|---|---|---|---|
| | | 1 | 2 | 3 | 4 | 5 | 6 | 7 | 8 | 9 | 10 | |
| 1 | VP 20 (Deg.) (2% Aqueous dispersion R 805) - Unstained | 0 | 0 | 0 | 0 | 1 | 0 | 0 | 0 | 0 | 0 | 1 |
| 2 | Tree Bark <45 10 g, Aerosil R 805 10 g, H$_2$O 380 g - Unstained | 1 | 0 | 1 | 1 | 5 | 4 | 0 | 0 | 0 | 0 | 12 |
| 3 | Tree Bark <45 10 g, Aerosil R 805 10 g, H$_2$O 380 g - Stained | 0 | 0 | 5 | 0 | 0 | 0 | 0 | 0 | 0 | 0 | 5 |
| 4 | Peat moss <45 10 g, Aerosil R 805 10 g, H$_2$O 380 g - Stained | 9 | 2 | 9 | 4 | 4 | 11 | 0 | 3 | 1 | 2 | 45 |
| 5 | Tree Bark <120 5 g, Aerosil R 805 5 g, H$_2$O 190 g - Stained | 9 | 0 | 1 | 1 | 0 | 2 | 0 | 1 | 0 | 0 | 14 |
| 6 | Tree Bark <45 5 g, H$_2$O 195 g - Unstained | 0 | 5 | 16 | 27 | 17 | 12 | 21 | 13 | 13 | 14 | 138 |
| 7 | Peat moss <45 10 g, Aerosil R 805 10 g, H$_2$O 380 g - Unstained | 0 | 2 | 0 | 0 | 1 | 0 | 1 | 0 | 0 | 1 | 5 |
| 8 | Peat moss <45 5 g, H$_2$O 195 g - Unstained | 0 | 24 | 6 | 13 | 28 | 10 | 13 | 10 | 19 | 18 | 141 |
| 9 | Controls - (Untreated Medium) | 55 | 60 | 39 | 19 | 2 | 6 | 15 | 19 | 10 | 12 | 237 |
| 10 | Insects Migrating Freely | 23 | 4 | 19 | 32 | 39 | 53 | 42 | 38 | 28 | 19 | 297 |
| 11 | Accumulated Death Rate | 0 | 2 | 2 | 2 | 5 | 8 | 8 | 16 | 29 | 34 | 34 |

*)Tribolium Confusum Duv. (Deprived for 5 days)
**)DRY FLOUR CAKES:
Prepared by mixing 80 g of whole wheat flour with 50 g of distilled water.
After 24 hr. dessication, the weight of a single cake = 3.0 g (1.5 mm thick).

The effect of aqueous dispersions of certain spices on deterring insects was also studied, and the results are summarized in Table 7.

TABLE 7

NUMBER OF INSECTS (TRIBOLIUM CONFUSUM DUV.) SETTLED ON DRY FLOUR CAKES*) TREATED WITH SPICES
(100 INSECTS USED)

| | SPICE TESTED (10% AQUEOUS SUSPENSION) | DAY | | | | | |
|---|---|---|---|---|---|---|---|
| No. | ON DRY FLOUR CAKES*) | 1 | 2 | 3 | 4 | 5 | TOTAL |
| 1 | CAYENNE | 6 | 1 | 1 | 0 | 0 | 8 |
| 2 | CORIANDER | 0 | 0 | 0 | 1 | 0 | 1 |
| 3 | CUMIN | 0 | 0 | 0 | 0 | 0 | 0 |
| 4 | CURRY | 0 | 0 | 0 | 0 | 0 | 0 |
| 5 | NUTMEG | 0 | 0 | 1 | 17 | 9 | 27 |
| 6 | CONTROL (Untreated Cake) | 9 | 10 | 17 | 7 | 24 | 67 |
| 7 | ROAMING INSECTS | 85 | 89 | 81 | 75 | 67 | — |

*)DRY FLOUR CAKES
Prepared by mixing 80 g of whole wheat flour with 50 g of distilled water. After 24 hr. dessication, the weight of a single cake = 3.0 g (1.5 mm thick).

It was observed that the spices tested had the effect of significantly deterring insects from the dry flour cakes treated, relative to the untreated controls. The spices are useful ingredients in aqueous dispersions according to the invention.

The aqueous dispersions of the invention can be used for the purpose of insect control in agriculture, horticulture, silviculture (forestry), human and veterinary medicine, the construction industry and so on. The dispersions are applied in sufficient amounts to the substrates, eg. plant surfaces, until a visible and continuous layer is formed. They can conveniently be applied by spraying, using conventional liquid spraying equipment. The dispersions should be shaken before use to assure uniformity, and if necessary during the application, if separation of the dispersion occurs.

The dispersions can be applied to the ground to control insects in their developmental stages in the soil. Preferably, they are applied to a depth of about 2–5 cm, and form a protective layer preventing insects larvae from attacking plant roots, bulbs and tubers. Application to the ground can be by spraying or pouring.

I claim:

1. A composition for killing or deterring insects comprising a dispersion of:
   (a) a particulate, hydrophobic insecticidal or insect-deterring;
   (b) a hydrophilic substance having the properties of (i) increasing the physico-chemical stability of said dispersion and (ii) modifying the textural, visual, and/or olfactory characteristics of surfaces to which said composition is applied, wherein said hydrophilic substance is solid and finely-divided before addition to said dispersion; and
   (c) water.

2. A composition according to claim 1 wherein the particle size of component (a) is 5–40 nanometers.

3. The composition according to claim 1 wherein said hydrophobic silica has the following characteristics:
   Surface area: 70 to 290 m$^2$ per g
   Average particle size: 5–40 nanometers
   pH: 3.4–7.5.

4. The composition according to claim 1 wherein component (b) is organic.

5. The composition according to claim 4 wherein component (b) is at least one member selected from the group consisting of finely-divided bagasse, bark, bone meal, burlap, casein, charcoal, cellulose, cork, duff, cotton wool, feathers, leaves, non-fat powdered milk, paper, peat moss, pumice, tang, sawdust, seaweed, straw, whey, yeast, wood flour, starch, and oyster shells.

6. The composition according to claim 4 wherein component (b) is pine bark flour.

7. The composition in accordance with claim 4 wherein component (b) is fibrous.

8. The composition according to claim 4 wherein component (b) is peat moss.

9. The composition in accordance with claim 4 wherein component (b) is shredded paper.

10. The composition in accordance with claim 4 wherein component (b) is a powder.

11. The composition in accordance with claim 10 wherein component (b) has a particle size of less than 355 µm.

12. The composition in accordance with claim 10 wherein component (b) has a particle size of less than 120 µm.

13. The composition according to claim 1 wherein component (a) comprises about 2–3% by weight of said dispersion.

14. The composition according to claim 1 wherein component (b) comprises about 2–5% by weight of said dispersion.

15. The composition in accordance with claim 1 further comprising one or more components having the property of modifying the smell and/or color of the composition after drying.

16. The composition in accordance with claim 15 further comprising at least one member selected from the group consisting of sage, curry, allspice, thyme, anise, cinnamon, oregano, cloves, ginger, black pepper, chili, celery seed, nutmeg, dill seed, onion, garlic, horse radish, cayenne, green pepper and coloring agent.

17. A method of rendering an environment uninhabitable by insects, comprising introducing an effective amount of the composition as defined in claim 1 into said environment.

18. The composition according to claim 1 wherein component (b) is inorganic.

19. The composition according to claim 18 wherein component (b) is selected from the group consisting of fuller's earth, bentonite, sparcoloid, talc, kaolin, Alberta slip, silica flint, bone ash, Edgar Plastic Kaolin, dolomite, pyrophilite, Old Mining #4 ballclay, volcanic ash, nepheline syenite, calcium carbonate, cluster feldspar, pumice, chalk, vermiculite, and diatomaceous earth.

20. The composition according to claim 18 wherein component (b) is diatomaceous earth.

21. A method of killing or deterring insects comprising the steps of
   (a) providing an aqueous dispersion comprising
      (i) a particulate, hydrophobic insecticidal or insect-deterring silica
      (ii) a hydrophilic substance having the properties of increasing the physico-chemical stability of said dispersion and modifying the textural, visual and/or olfactory characteristics of surfaces to which said composition is applied, wherein said hydrophilic substance is solid and finely-divided before addition to said dispersion; and
      (iii) water;
   (b) applying said dispersion to a substrate; and
   (c) allowing said dispersion to become desiccated.

22. The method in accordance with claim 21 wherein said dispersion is applied to plant surfaces by spraying.

* * * * *